United States Patent [19]

Uchigaki et al.

[11] Patent Number: 5,038,021

[45] Date of Patent: Aug. 6, 1991

[54] ANALYZING DEVICE

[75] Inventors: Takatoshi Uchigaki, Kyoto; Yoshito Komada, Nara; Yasumitsu Takagi, Takatsuki, all of Japan

[73] Assignee: Kyoto Daiichi Kagaku Co., Ltd., Kyoto, Japan

[21] Appl. No.: 514,932

[22] Filed: Apr. 26, 1990

[30] Foreign Application Priority Data

Apr. 27, 1989 [JP] Japan .................................. 1-109539

[51] Int. Cl.⁵ ...................... G06F 15/20; G01N 27/26
[52] U.S. Cl. ...................... 235/375; 204/416
[58] Field of Search ............... 235/375, 454; 204/406, 204/412, 416

[56] References Cited

U.S. PATENT DOCUMENTS

| | | | |
|---|---|---|---|
| 4,257,862 | 3/1981 | Schnipelsky et al. | |
| 4,279,861 | 7/1981 | Jessop | |
| 4,321,122 | 3/1982 | Whitcomb | 204/400 X |
| 4,613,420 | 9/1986 | Seshimoto | 204/406 X |
| 4,655,899 | 4/1987 | Saito | 204/416 |
| 4,797,193 | 1/1989 | Uekusa et al. | |

FOREIGN PATENT DOCUMENTS

| | | |
|---|---|---|
| 0154147 | 9/1985 | European Pat. Off. |
| 0285851 | 10/1988 | European Pat. Off. |
| 62-174650 | 7/1987 | Japan |
| 62-165147 | 8/1987 | Japan |

*Primary Examiner*—Harold Pitts

[57] ABSTRACT

An analyzng device comprises a plate holding table, a shifting mechanism for shifting the plate holding table, bar code reading sensors, and a detecting unit for detecting the signals based on the drops of the solutions in the plate set on the plate holding table located in the plate measurement position. When the data of the bar code read by the bar code reading sensor is not fit for a predetermined measurement condition, the plate holding table is shifted to the plate exhausting position. On the other hand, when the data of the bar code is fit for the predetermined measurement condition, the plate holding table is shifted to the solution pipetting position and when the pipetting of the solutions is finished, the plate holding table is further shifted to the mesurement position. When the concentration of substance in the test solution is completed by the detecting unit, the plate holding table is shifted to the plate exhausting position.

9 Claims, 10 Drawing Sheets

ANALYZING DEVICE

BACKGROUND OF THE INVENTION

1. Field of the Invention

The present invention relates to a semi-automatic analyzing apparatus using an analyzer for analyzing a solution or liquid, in particular to an analyzing apparatus in which drops of test solution and standard solution are individually spotted on elements formed on a plate member and a substance concentration such as an ion concentration of the test solution is detected by a signal detected on the basis of the spotted solutions.

2. Description of the Prior Art

Figure 1:
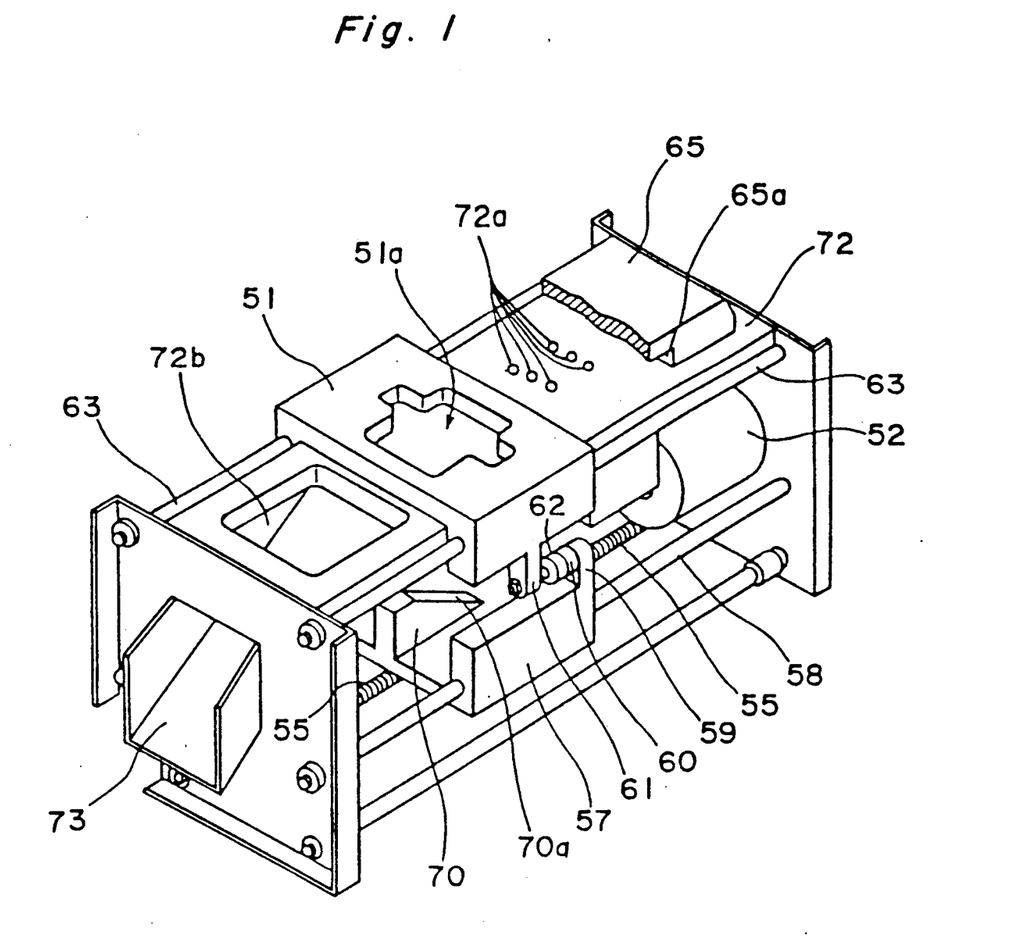
FIGS. 1 and 2 are perspective and sectional views of the conventional analyzing device.
Figure 2:
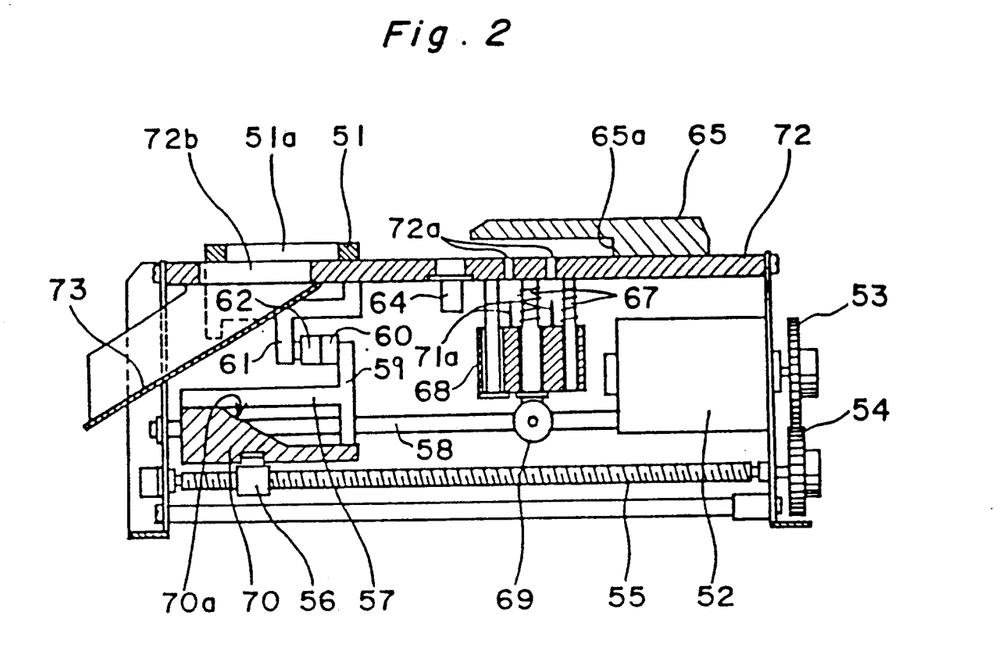
Figure 3:
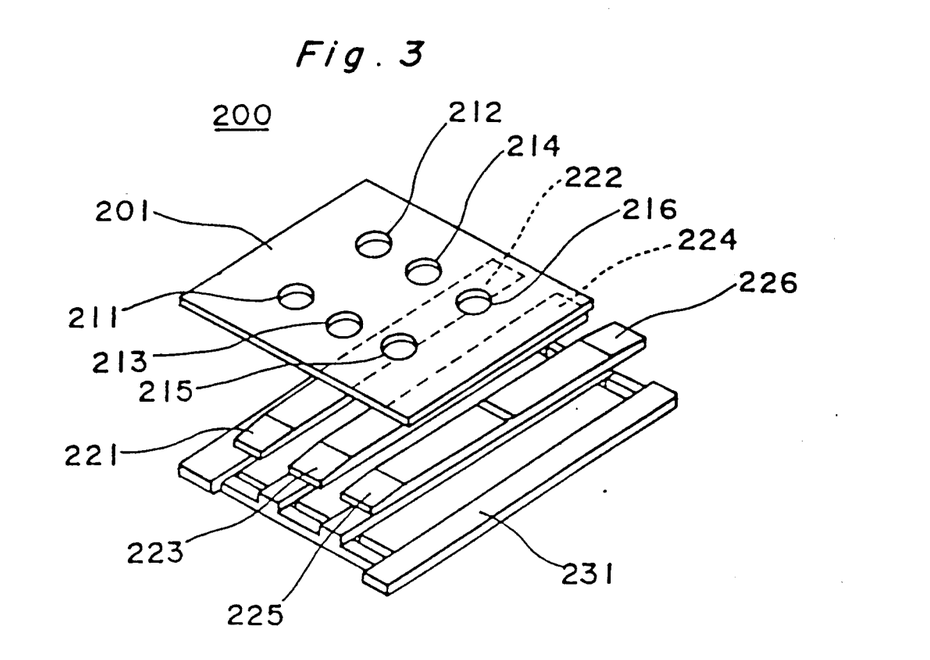
FIG. 3 is an exploded perspective view showing a structure of a plate used in the analyzing device shown in FIGS. 1 and 2.

As an example of this kind of analyzer, the explanation is made about an ionic activity measuring analyzer disclosed in the Japanese Patent Laid Open 62-165147 with reference to FIGS. 1 to 3.

FIGS. 1 and 2 show a perspective view and a sectional view of a driving mechanism portion for shifting a plate member to a predetermined measurement position and FIG. 3 shows an exploded perspective view of plate members used in the analyzer.

As shown in FIG. 3, the plate member 200 comprise a water impermeable upper substrate 201 having three pairs of solution receiving holes 211-212, 213-214 and 215-216 for receiving a test solution and standard solution in order to measure three kinds of ion concentrations (such as Na+, K+ and Cl−); a lower supporting frame 231; and three pairs of strip shaped electrodes 221-222, 223-224 and 225-226 provided between the substrate 201 and the lower supporting frame 231, in other words, provided under the substrate 201 corresponding to the positions of the respective solution receiving holes 211 to 216 and on the lower supporting frame 231. In a predetermined portion on the underside surface of the lower supporting frame 231, there are depicted bar codes (not shown) for representing test items of the plate member 200 and batch data of the plate member 200 In addition, although there are provided pouring members on the substrate 201 for charging the test solution into the solution receiving holes 211, 213 and 215 and for charging the standard solution into the solution receiving holes 212, 214 and 216, the explanation thereof is omitted.

In this plate member 200, when a drop of the test solution is spotted in the solution receiving hole 211 and a drop of the standard solution is spotted in the solution receiving hole 212, there is generated electric power based on the ionic activities contained in the respective test and standard solutions disposed in the solution receiving holes 211 and 212 so that there occurs potential different between the electrodes 221 and 222 corresponding to the solution receiving holes 211 and 212 respectively. Therefore, by measuring the above difference of potential between the electrodes 221 and 222, the Na+ ion concentration of the test solution can be detected on the basis of calibrations predetermined by using a known Na+ ion solution.

Next, the structure and operation of the conventional analyzer mentioned above are explained with reference to FIGS. 1 and 2. Under the condition that the plate member 200 is set in a setting opening 51a defined in a central portion of a holder 51, there are spotted drops of blood as a test solution for example in the respective solution receiving holes 211, 213 and 215 formed in the plate member 200 and there are spotted drops of standard ion concentration solution of Na+, K+ and Cl− in the solution receiving holes 212, 214 and 216. And when a predetermined button switch (not shown) is turned on, a motor 52 is driven so as to rotate a rod screw 55 by rotating a pair of engaged gears 53 and 54. By this rotation of the rod screw 55, a female screw member 56 engaged with the rod screw 55 as a male screw is shifted to the right direction along the axis of the rod screw 55, whereby a holder shifting table 57 coupled with the female screw 56 as one body is shifted to the right along a pair of guide members 58. On a left surface of a connecting member 59 projected upward from a predetermined portion of the holder shifting table 57, there is fixed a magnet member 60. Similarly, on a right surface of a connecting member 61 projected downward from a predetermined portion of the holder 51, there is fixed a magnet member 62 abutting to the magnet 60. Therefore, when the holder shifting table 57 is shifted, the holder 51 is similarly slid along a pair of guide members 63 due to the attraction between the two magnet members 60 and 62.

In such a manner as described above, the plate member 200 set in the opening of the holder 51 is shifted together with the holder 51, and when the bar code depicted on the underside surface of the lower supporting frame 231 of the plate member 200 is passed by a position above a bar code reading sensor 64, the bar code is read by the bar code reading sensor 64 which is provided in the central portion under the top plate member 72 of the driving mechanism. The batch data of the bar code are used for correcting the calibrations which are applied for measuring an ion concentration of a solution to be described later.

The holder 51 with the plate member 200 set therein is further slid to the right, and when the right edge portion of the holder 51 is abutted to a left side wall of a stopper portion 65a of a plate depressing member 65, the holder 51 is stopped at this position, but since the motor 52 is still being driven, the magnets 60 and 62 for attracting the holder 51 and the holder shifting table 57 are separated from each other so that only the holder shifting table 57 is shifted to the right.

There is situated a probe holder 68 pushed downward by a spring member 67 in a position below the measurement position of the plate member 200 set in the holder 51 when the holder 51 is stopped by abutting to the holder stopper portion 65a and there is fixed a roller 69 attached to the bottom portion of the probe holder 68. On the other hand, in a predetermined portion of the holder shifting table 57, there is provided a cam member 70 having a right side surface 70a sloped with a predetermined degree, and since the sloped side surface 70a of the cam member 70 is abutted to the roller 69 when the holder shifting table 57 is shifted to the right, the roller 69 together with the probe holder 68 are pushed upward. Consequently, six contact pins 71a fixed on the upper surface of the probe holder 68 are inserted through six holes 72a defined in the top plate member 72 so as to be abutted to the respective electrodes 221 to 226 of the plate member 200, thereafter the motor 52 is stopped. In this state, the difference of potential between the drop of the test solution and the drop of the standard solution disposed in the plate member 200 are detected through the six contact pins 71a. The time period from the drop of the solution onto the plate member 200 to the start of the detection of the difference of potential is predetermined to be one minute and the detection of the difference of potential is carried out in about one minute.

When the detection of the difference of potential is completed, the motor is reversed and the holder shifting table 57 is slid to the left, so that the probe holder 68 is pushed down to the first set position and the contact pins 71a are drawn apart from the electrodes of the plate member 200. When the holder shifting table 57 is further slid to the left, the magnet 60 fixed to the projected portion 59 of the holder shifting table 57 is abutted to the magnet 62 fixed to the projected portion 61 of the holder 51, thereafter the holder 51 having the plate member 200 set therein is shifted from the measurement position to the left as the holder shifting table 57 is shifted to the left. When the holder 51 is shifted to the left end discharge position, the measurement finished plate 200 set in the holder 51 drops down through an opening 72b defined in the left portion of the top plate member 72 so as to be discharged through an exhauster.

As described above, in this conventional analyzer device, after the drops of the solutions are disposed in the plate 200, the bar code depicted on the underside of the plate 200 is read by the bar code reading sensor 64. Therefore, even in the cases that, a plate 200 for measuring other kinds of ion concentration than that of the ion concentration to be measured is set, a plate 200 of other batch than the predetermined batch registered in the device is set, or a plate 200 is set in the inverted direction, it is not found that the measurement is unavailable until the bar code is read by the bar code reading sensor 64 after the drops of the test solutions are disposed in the plate 200. Since the plate 200 having drops of solutions disposed thereon can not be used once more, the plate 200 is spoiled. Moreover, when such a miss of the measurement is found, since the plate 200 has been shifted to the measurement position, there is a fault that it takes much time to shift the plate 200 back to the start position, resulting in deterioration of the working efficiency.

SUMMARY OF THE INVENTION

The present invention has been made in order to solve the problem mentioned above and has its essential object to provide an analyzing device in which a mis-set plate for a plate to be used for measurement can be found before disposing drops of solutions in the plate, thereby improving the working efficiency.

According to the feature of the present invention, an analyzing device for measuring a concentration of an objecting substance in a test solution based on a signal generated by the test solution dropped on a unit formed on a plate which is disused after once usage thereof or for measuring based on a difference between a signal generated in the test solution and a signal generated in a standard solution comprises;

a plate holding table in which said plate is set in a plate setting position;
  a shifting mechanism for shifting said plate holding table in a predetermined direction;
  one or more bar code reading sensors which read data of a bar code depicted on the plate before said plate holding table is shifted to the pipetting position and said drops of the solutions are pipetted on the plate;
  a detecting unit for detecting the signals based on the drops of the solutions in the plate set in the plate holding table situated in the plate measurement position for measuring the detected signals; and
  control means for controlling the shifting mechanism in such a manner that, when the data of the bar code read by the bar code reading sensors are not fit for a predetermined measurement condition, the plate holding table is shifted to the plate exhausting position for exhausting the plate set in the plate holding table, on the other hand, when the data of the bar code read by the bar code reading sensors are fit for the predetermined measurement condition, said plate holding table is shifted to the solution pipetting position and when the pipetting operation of the solutions is finished, the plate holding table is further shifted to the measurement position and when the concentration of the substance in the test solution is completed by the detecting unit, the shifting mechanism is so controlled as to shift the plate holding table to the plate exhausting position.

In the analyzing device according to the present invention, after the plate is set in the plate holding table in the plate setting position, the plate holding table is shifted to the solution pipetting position and the data of the bar code of the plate is read by the bar code reading sensor before the solution pipetting operation is started. At this time, when it is judged that the the bar code data of the plate read by the bar code reading sensor is not fit for the measurement condition of the analyzing device, an error display is performed or the plate holding table is immediately shifted to the plate exhaust position so as to exhaust the plate. On the other hand, when the bar code data is fit for the predetermined measurement condition, the solution spotting operation is performed at this pipetting position, and subsequently the plate holding table is shifted to the measurement position, and the concentration of the solution is detected on the basis of the signals detected from the unit on the plate by the detecting unit. When the detection of the concentration of the solution is finished, the plate holding table is shifted to the plate exhaust position.

The novel features believed to be characteristic of the invention are set forth with particularity in the appended claims. The invention itself, however, as well as further objects and advantages thereof may best be understood with reference to the following detailed description, when read in conjunction with the accompanying drawings which are given by way of illustration only, and thus are not limitative of the present invention.

DETAILED DESCRIPTION OF THE PREFERRED EMBODIMENT

An embodiment of an analyzing device of the present invention will be explained with reference to FIGS. 4 to 14. Before the explanation proceeds, it is noted that like parts are designated by like reference numerals in FIGS. 4 to 14.

Figure 4:
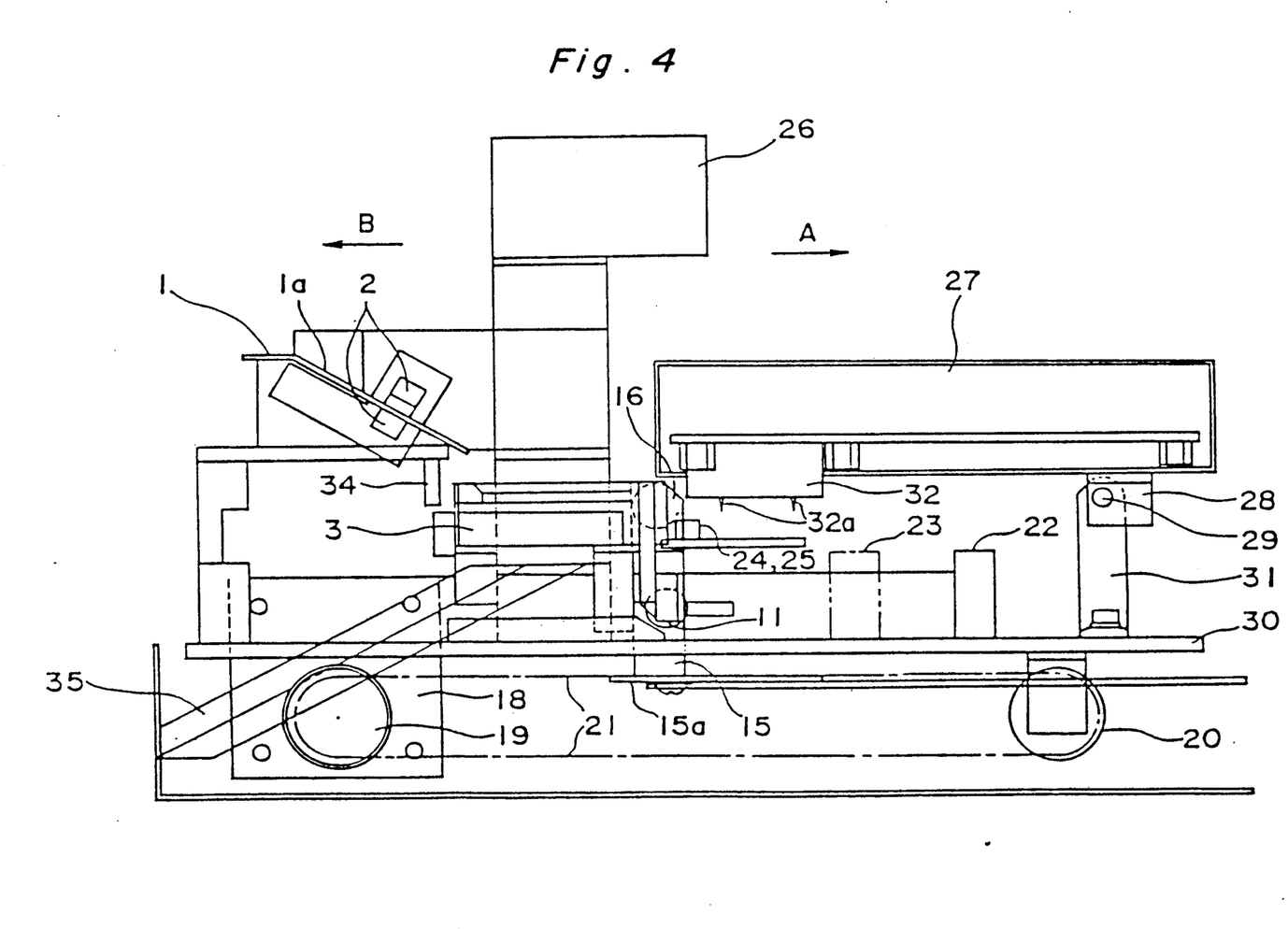
FIG. 4 is a side view showing an embodiment of a analyzing device according to the present invention.
Figure 5:
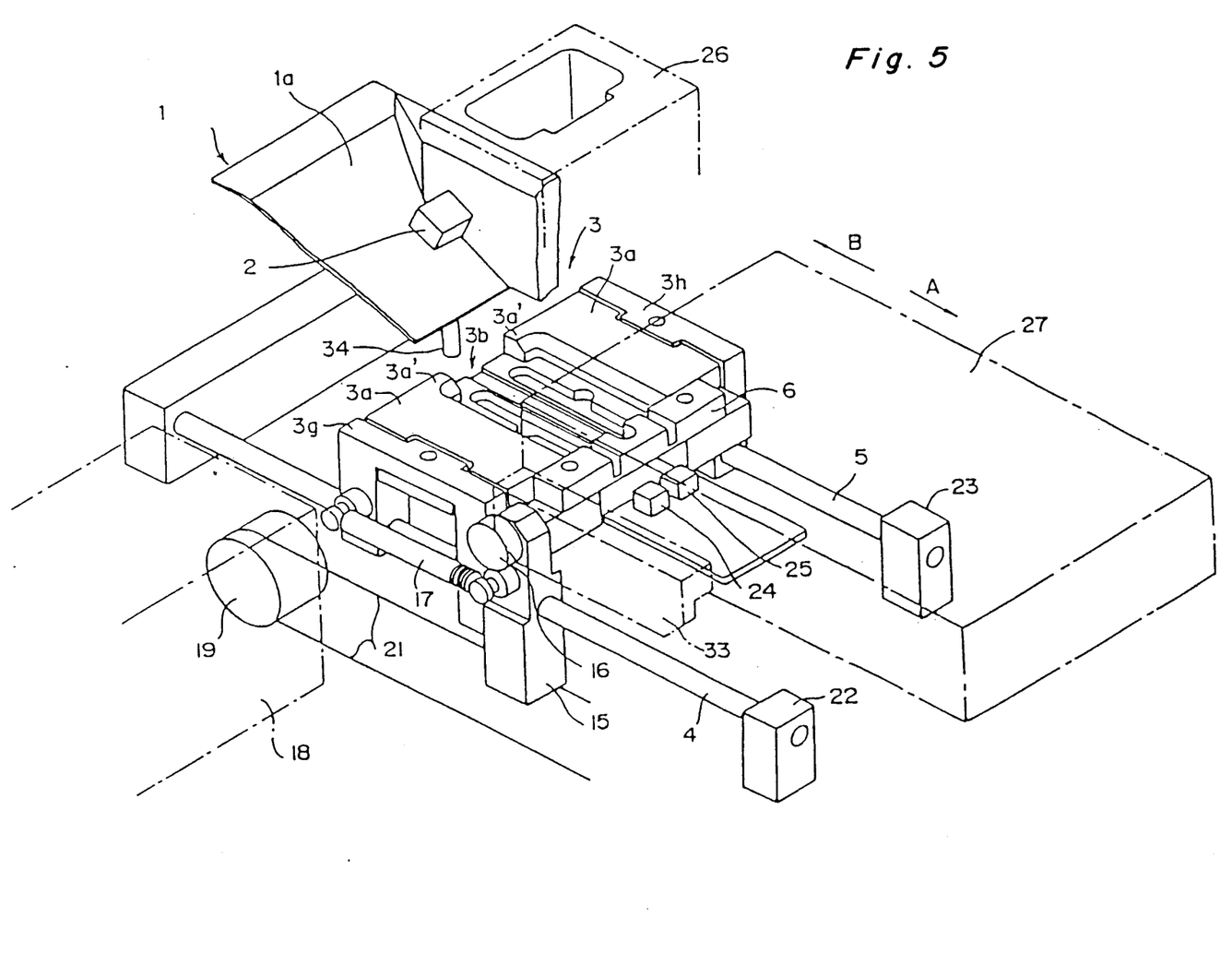
FIG. 5 is a perspective view showing a shifting mechanism for use in the analyzing device shown in FIG. 4.
Figure 6:
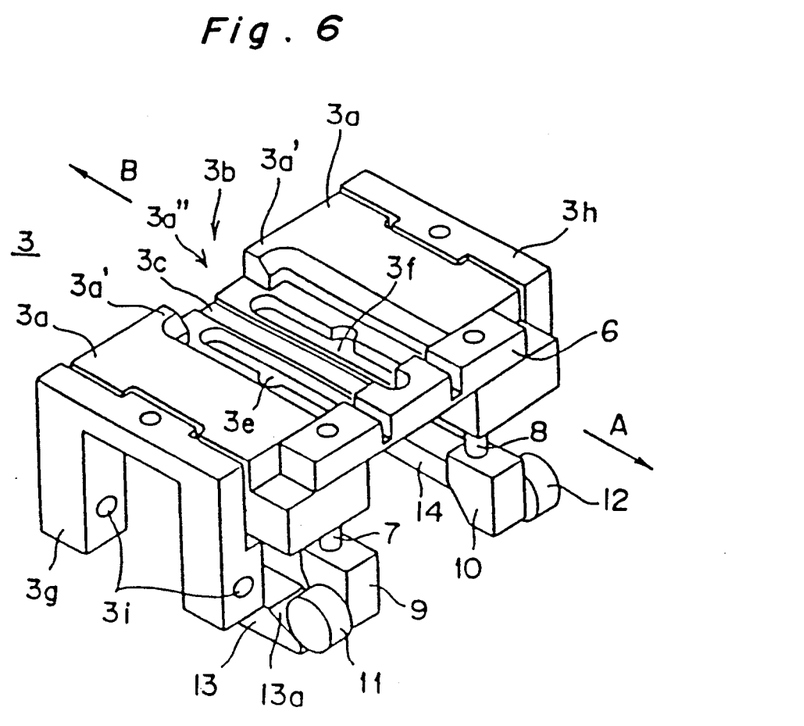
FIG. 6 is a perspective view showing a plate shifting portion shown in FIG. 5.

As shown in FIGS. 4 to 6, reference numeral 1 denotes an inlet shooter having a sloped surface 1a for slidingly feeding a plate with a sample solution for testing into the analyzing device, and reference numeral 2 denotes a photosensor for detecting the feed of the plate in the inlet shooter 1.

Figure 7:
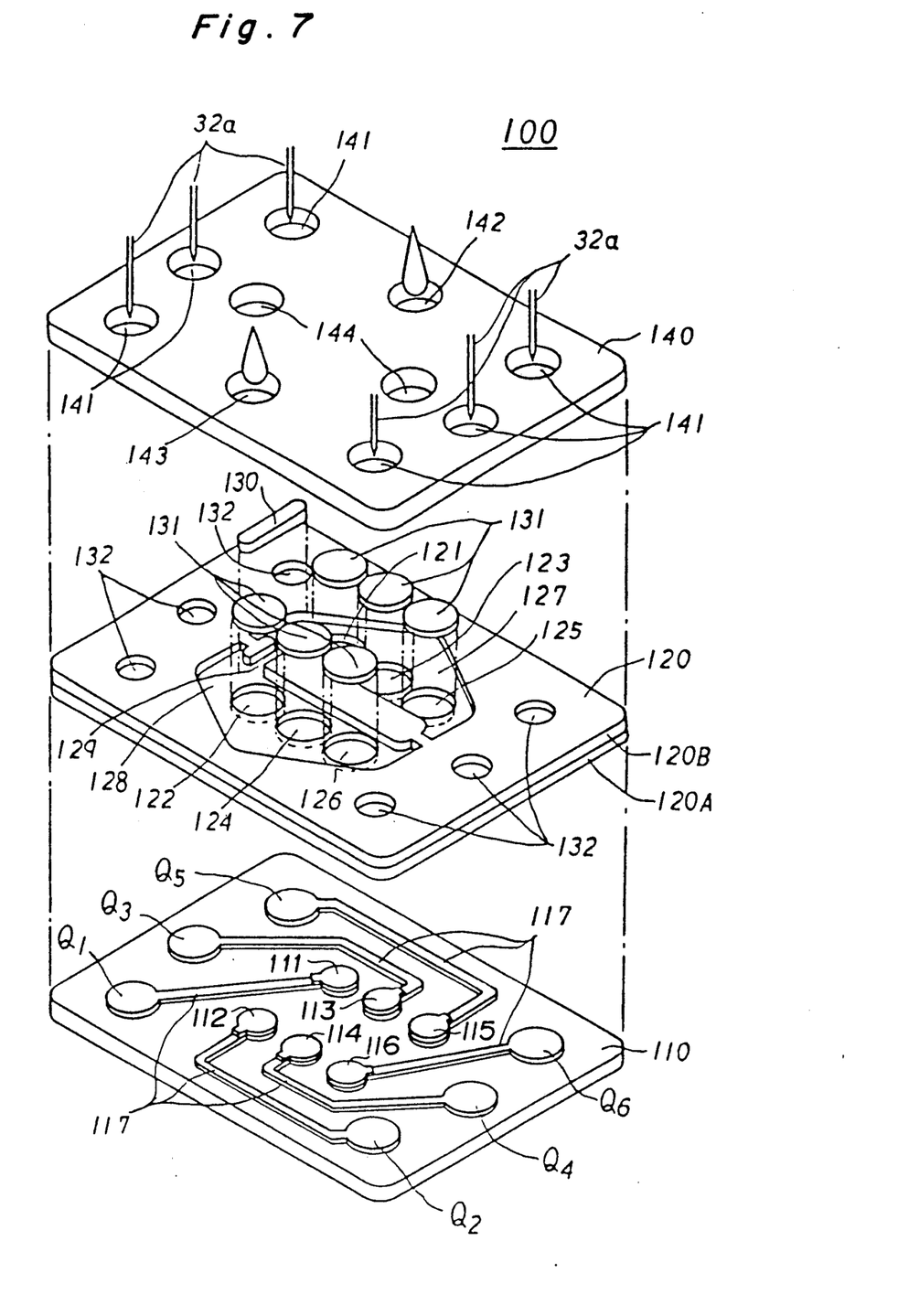
FIG. 7 is an exploded perspective view showing a plate used in the analyzing device shown in FIG. 4.

As shown in FIG. 7, a plate 100 for use in the analyzing device comprises an insulator base film 110, an intermediate resist film 120 and a covering film 140.

On the base film 110, there are provided three pairs of solution receiving vessels 111-112, 113-114 and 115-116 for receiving a test solution and a standard solution for measuring three kinds of ion concentrations such as $Na^+$, $K^+$ and $Cl^-$ of the test solution. And there are provided six electrode elements 117 made of Ag layers each extending from the solution receiving vessels 111-116 to terminal portions $Q_1$-$Q_6$ and there are also formed AgCl layers on the solution receiving vessels 111 to 116.

The intermediate resist film 120 is composed of two films, i.e., an lower half 120A and an upper half 120B. In the lower half 120A there are formed six holes 121 to 126 corresponding to the solution receiving vessels 111 to 116. In the upper half 120B, two openings 127 and 128 are formed with said opening 127 including the holes 121, 123 and 125 and said opening 128 including the holes 122, 124 and 126. The opening 127 is led to the opening 128 through a cut slot 129. There is provided a bridge member 130 for leading a solution and there are provided ion selective membranes 131 on the respective holes 121 to 126 for selecting each of the ions such as $Na^+$, $Cl^+$ and $K^+$. Moreover, there are formed six through holes 132 in both of the lower and upper halves 120A and 120B corresponding to the terminal portions $Q_1$ to $Q_6$ provided on the base film 110.

In the top covering film 140, there are formed six through holes 141 corresponding to the six through holes 132 formed in the resist film 120 and there are also formed two through holes 142 and 143 for feeding drops of the test solution and standard solution into the two openings 127 and 128 formed in the resist film 120. A pair of through holes 144 are also formed for discharging air in the openings 127 and 128 defined in the resist film 120 when the drops of the solution are fed from the solution feeding holes 142 and 143. Reference numerals 32a denote contact pins, which are inserted through the holes 141 and 132 defined in the top covering film 140 and intermediate resist film 120 respectively and is in contact with the terminal portions $Q_1$ to $Q_6$ provided on the base film 110. Moreover, there is depicted a bar code on the underside surface of the base film 110.

Figure 8:
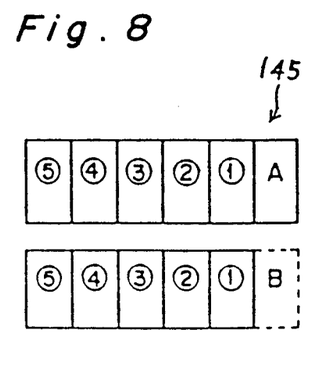
FIG. 8 is a view showing a bar code depicted on the underside surface of the plate.

As the bar code data, there are data such as a data representing a kind of a plate, a batch data and data representing the direction and the right side and wrong side of the plate, therefore, it is required to provide a lot of bar codes. However, since the area of the plate 100 is generally 2 cm×3 cm, the width of the bar codes must be fine so that it is required to provide a highly sensible sensor for reading the bar code, resulting in raising the cost of the device. Therefore, in the present invention, as shown in FIG. 8, by providing a bar code 145 of two lines, each of the bars may be wider so that it is not required to provide a highly sensible sensor and the cost is lowered by providing two cheap sensors. In the bar code 145 of two lines as shown in FIG. 8, the head bits A and B are applied for detecting the direction of the plate 100 and there can be stored 32 kinds of measurement data by the combination of the two lines of the five bits (1) to (5).

Referring to FIGS. 4 to 7 again, reference numeral 3 denotes a plate holder for receiving the plate 100 fed through the inlet shooter 1 in a predetermined plate setting position and for shifting the plate to one or more predetermined measurement positions. The plate holder 3 is described in detail with reference to FIG. 6. Herein, the directions shown by arrow marks A and B are referred to as forward and backward directions of the plate holder 3. The plate holder 3 comprises a plate placing member 3a of a horizontal plane member having a plate setting recess 3b formed in the center portion thereof for holding the plate 100. One end side portion of the plate setting recess 3b is opened in order to remove the plate 100 set in the plate setting recess 3b in the forward direction A. While, in the other end side portion of the plate setting recess 3b, there are formed a pair of stopper members 3a' by projecting rear end portions of the plate placing members 3a inwardly for preventing the plate 100 from slipping out of the plate setting recess 3b in the backward direction B. However, there is defined a cutting portion 3a'' between the stopper members 3a' in order that pin member for removing the plate is passed through the central portion of the plate setting recess 3b in the movement direction of the plate holder 3, and there is also formed a slot 3c in the central portion of bottom surface of the plate setting recess 3b in the movement direction of the plate holder 3. Moreover, there are formed a pair of bar code reading holes 3e and 3f in both sides of the slot 3c in the bottom of the plate setting recess 3b for reading the bar code of two lines depicted on the underside of the plate 100 set in the plate setting recess 3b.

Reference numerals 3g and 3h denote side wall members of U character shape provided on both sides of the plate placing member 3a and there are formed through holes 3i in the leg portions of the side wall members 3g and 3h in order that two guide rods 4 and 5 extending in the movement direction of the plate holder 3 are inserted through the holes 3i, whereby the plate holder 3 can be slidably shifted in the forward and backward directions along the guide rods 4 and 5. In addition, there are formed spaces between both side walls of the plate placing member 3a and the side wall members 3g and 3h so that the plate placing member 3a can be held in condition so as to be pushed downward.

Reference numeral 6 denotes a stopper member which is attached to the opening end portion of the forward side of the plate placing member 3a for preventing the plate 100 from getting out of the plate setting recess 3b to the direction A and the stopper member 6 is fixed to the top portions of guide shafts 7 and 8 which are vertically inserted through predetermined portions of the plate placing member 3a and there are provided rollers 11 and 12 on the lower end portions of the guide shafts 7 and 8 through predetermined attachment members 9 and 10 respectively.

Reference numerals 13 and 14 denote cam members (not shown in FIG. 4) provided in the device body in the movement direction of the plate holder 3 and the cam members 13 and 14 have end surfaces 13a and 14a formed to be sloped surfaces in the side of the direction A, and when the plate holder 3 is shifted backward and the rollers 11 and 12 are abutted onto the sloped surfaces 13a and 14a, the stopper member 6 together with the rollers 11 and 12 is lifted up, resulting in the end portion of the plate setting recess 3b being opened and the plate 100 can be removed.

Next, as shown in FIGS. 4 and 5, reference numeral 15 denotes a measurement portion lifting member for lifting a measurement portion, which is provided in the forward front side of the plate holder 3 and the central portion of the lifting member 15 is inserted by the guide shaft 4 and there is provided a roller 16 on the front side of the upper portion of the lifting member 15. A spring member 17 is bridged between a predetermined portion of the lifting member 15 and a predetermined portion of the side wall member 3g, whereby the side wall member 3g and lifting member 15 are integrally shifted as one body. Reference numeral 18 denotes a motor which is driven on the basis of the program control which will be described later and there is provided a belt 21 between a pulley 19 provided coaxially with the rotating shaft of the motor 18 and another pulley 20 provided in the side of the forward direction. A predetermined portion of the belt 21 and the bottom portion 15a of the lifting member 15 are fixed with each other.

Reference numerals 22 and 23 denote fixing members provided on the tops of the guide shafts 4 and 5 in the side of the forward direction, and the fixing member 22 acts as a stopper member against the lifting member 15 and the fixing member 23 acts as a stopper member against the side wall member 3h when the plate holder 3 is shifted to the forward direction. Reference numerals 24 and 25 denote bar code reading sensors for reading the bar code of two lines depicted on the underside of the plate 100 set in the plate setting recess 3b through the bar code reading holes 3e and 3f when the plate holder 3 is shifted to the forward direction. Reference numeral 26 denotes a pipet holder for holding a pipet, which is provided on the plate holder 3 set in the plate setting position as shown in FIGS. 4 and 5. A tandem type pipet 150 for use in the device is explained with reference to FIG. 9 as following.

Figure 9:
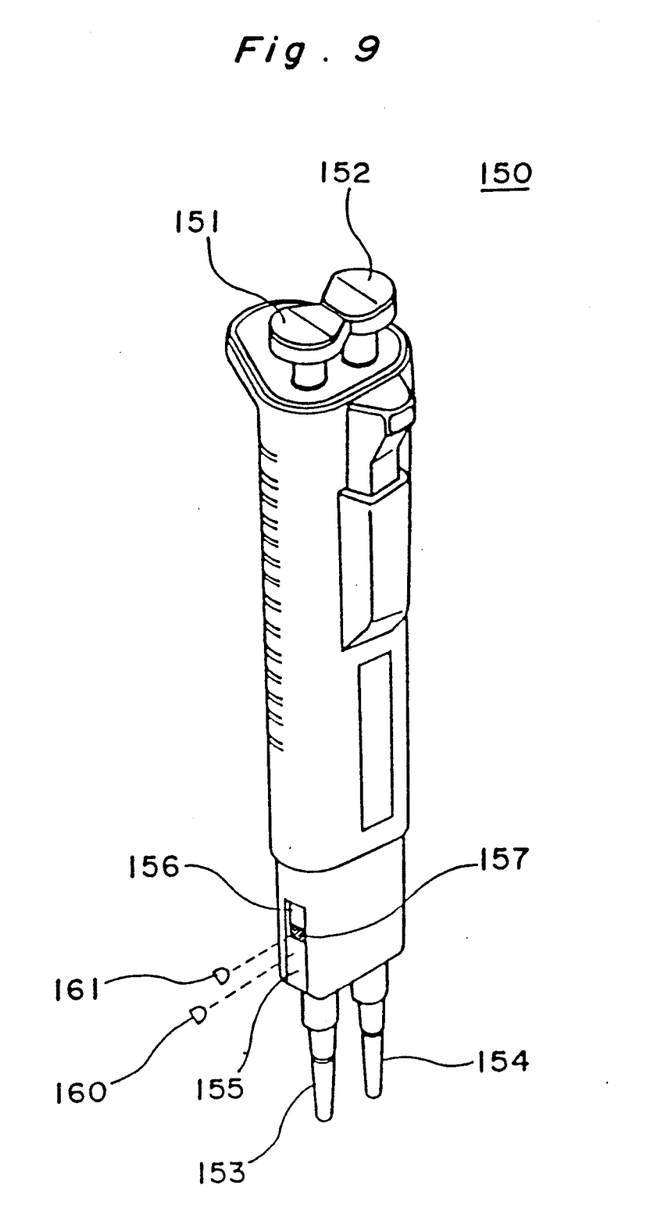
FIG. 9 is a perspective view showing a pipet used in the analyzing device of the present invention.
Figure 10:
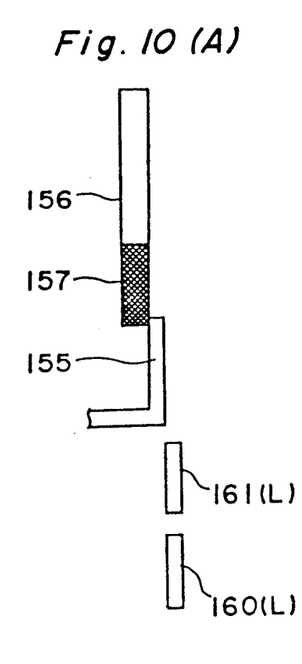
FIGS. 10(A) to 10(F) are views for explaining the normal spotting operation in the pipet shown in FIG. 9, and FIGS. 11 to 14 are schematic diagrams for explaining a series of operations in the analyzing device of the present invention.

There are provided operating buttons 151 and 152 on the top of the pipet 150, and when the operating buttons 151 and 152 are depressed and released by a finger, a test solution and standard solution are sucked in pipet tip portions 153 and 154. The pipet 150 containing the test solution and standard solution is installed in the pipet holder 26 and when the operating buttons 151 and 152 are depressed, the test solution and standard solution sucked in the pipet tips 153 and 154 are dropped onto the plate 100 set in the plate holder 3. Reference numeral 155 denotes a reflecting portion provided in a predetermined portion of the pipet 150 and reference numerals 156 and 157 are a reflecting portion and a black non-reflecting portion which are lowered down when the operating button 151 is depressed, and when in the normal condition, the non-reflecting portion 157 is situated between the reflecting portion 155 and the reflecting portion 156 and when the operating button 151 is depressed, the non-reflecting portion 157 is lowered down and is hidden behind the reflecting portion 155.

Reference numerals 160 and 161 denote photosensors for detecting the reflection rates of the reflecting portion 155 and non-reflecting portion 157 when the pipet 150 is set in the pipet holder 26. When the reflection rate of the reflecting portion 155 is detected by the photosensor 160, a H (high) level signal is generated, and when the reflection rate of the non-reflecting portion 157 is detected by the photosensor 161 and when the pipet 150 is pulled out, a L (low) level signal is generated. In the state as shown in FIG. 9, the photosensor 160 generates a high level signal and photosensor 161 generates a low level signal.

On the basis of the detection signals of H and L levels generated by the photosensors 160 and 161, it is detected whether or not the test and standard solutions are correctly pipetted on the plate 100 from the pipet 150 set in the pipet holder 26, and the operation thereof is explained with reference to FIGS. 10(A) to 10(F).

FIG. 10(A) shows a condition before the pipet 150 is installed in the pipet holder 26 and in this state, both photosensors 160 and 161 generate L level signals. FIG. 10(B) shows a condition when the reflecting portion 155 of the pipet 150 is passed by the position corresponding to the photosensor 161 in the process of setting the pipet 150 in the pipet holder 26, and at this time, the photosensor 161 generates a H level signal and the photosensor 160 generates a L level signal. FIG. 10(C) shows a condition when the pipet 150 is completely installed in the pipet holder 26, and in this state, the photosensor 160 detects the reflecting portion 155 and generates a H level signal, while the photosensor 161 detects the non-reflecting portion 157 and generates a L level signal. FIG. 10(D) shows a condition when the operating buttons 151 and 152 are depressed down in order to spot the drops of the test and standard solutions sucked in the pipet tips 153 and 154 in the pipet 150 onto the plate 100, and at this time, the non-reflecting portion 157 is lowered down and the reflecting portion 156 is faced to the photosensor 161, so that the photosensor 161 generates a H level signal. After the completion of the drop of the solutions, the pipet 150 is pulled out of the pipet holder 26 with the operating buttons 151 and 152 depressed down as shown in FIG. 10(E), and in this state, the photosensor 161 generates a H level signal and photosensor 160 generates a L level signal. FIG. 10(F) shows a condition when the pipet 150 is completely pulled out of the pipet holder 26, and in this state, both of the photosensors 160 and 161 generate L level signals.

In a series of the processes mentioned above, when the photosensors 160 and 161 generate the H and L level signals in the order as described above, it is judged by a central processing unit for controlling the analyzing device that the test and standard solutions are exactly dropped onto the plate 100 and the difference of potential is measured as to be described later. On the other hand, after the drop of the solutions as shown in FIG. 10(D) for example, if the pipet is pulled out with the operating buttons 151 and 152 released, the dropped solutions are sucked in the pipet tips 153 and 154 again. In this case, since the detection signals generated from the photosensors 160 and 161 are different from those in the normal operation as mentioned above, it is judged by the CPU that the drops of the solution is mistaken so that an error of a drop operation is displayed on a display unit (not shown).

Referring to FIGS. 4 and 5 again, reference numeral 27 denotes a measurement portion and reference numeral 28 denotes a metal fitting member of a U character shape provided in a predetermined portion under the measurement portion 27 in the side of the direction A. A shaft rod 29 is so inserted through the metal fitting member 28 that the measurement portion 27 is pivotally rotated around the shaft rod 29, which is pivotally supported by a shaft supporting member 31 provided on a predetermined portion of a bottom plate 30 of the analyzing device body. In a predetermined portion corresponding to the measurement position of the plate 100 in the side of the direction B under the measurement portion 27, there is provided a detecting unit 32 having six contact pins 32a projected downward in a predetermined portion thereof for contacting with terminal portions $Q_1$ to $Q_6$ respectively disposed in the plate 100. Also, there is fixed a cam member 33 of a reversedly trapezoid shape to one side portion of the measurement portion 27 as shown in FIG. 5. When the plate holder 3 is shifted to the forward direction, the cam member 33 is abutted to the roller 16 provided on the lifting member 15 so that the measurement portion 27 is pivotally lifted by a predetermined angle around the shaft rod 29. However, the measurement portion 27 is set in a horizontal state in a normal condition as shown in FIG. 4.

Reference numeral 34 denotes a plate removing pin which is abutted to one edge of the plate 100 set in the plate setting recess 3b when the plate holder 3 is further shifted to the backward direction from the plate setting position. Reference numeral 35 denotes a plate removing shooter through which the plate 100 is exhausted to the outside when the plate holder 3 is furthermore shifted to the backward direction to be set in the plate removal position.

The operation of the analyzing device of the present invention is explained with reference to FIGS. 11 to 14. It is noted that, in this analyzing device, the measurement condition such as the kind of the plate 100 and batch data thereof are previously registered in the analyzing device through a magnetic card.

Figure 11:
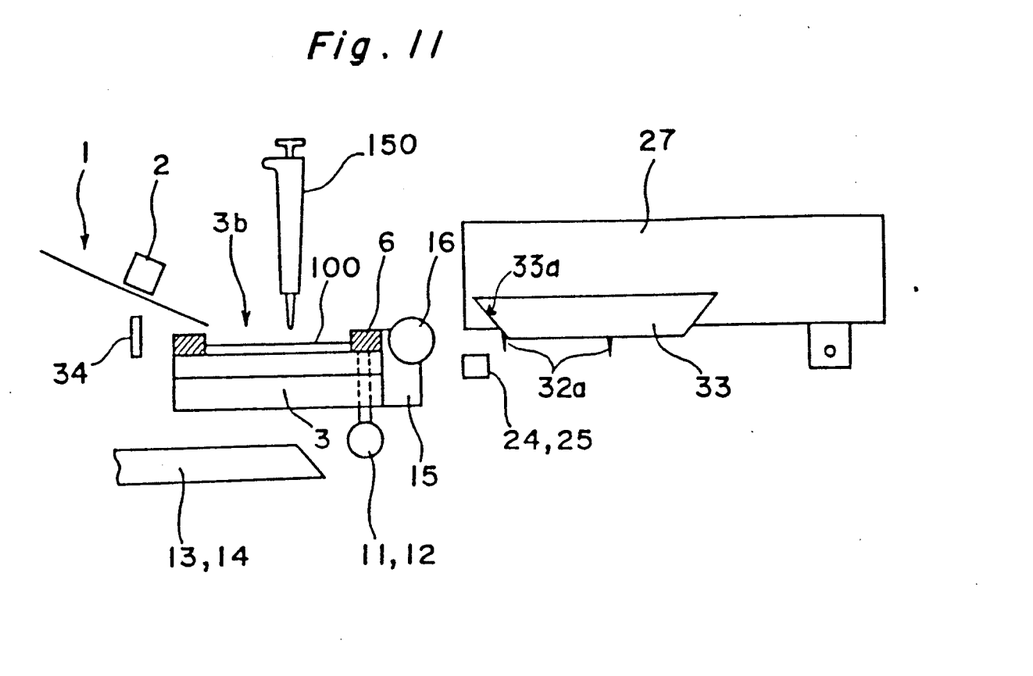

When the plate 100 is fed into the plate holder 3 situated in the plate setting position through the inlet shooter 1, the inserted plate 100 is set in the plate setting recess 3b as shown in FIG. 11. At this time, when the passage of the plate 100 is detected by a photosensor 2, the mode of the analyzing device is set in the measurement starting condition. And after a predetermined time lapse, the motor 18 is driven and the belt 21 is moved, so that the plate holder 3 forced to the lifting member 15 by the spring member 17 is shifted to the forward direction and when the front edge portion in the forward direction of the plate holder 3 is abutted to the fixing member 23, i.e., when the plate holder is set in the measurement position, the drive of the motor 18 is stopped as shown in FIG. 12.

At this time, the roller 16 fixed on the lifting member 15 is abutted to the first sloped end surface 33a of the cam member 33 under the measurement portion 27, so that the measurement portion 27 is slightly pivotally lifted around the pivot shaft 29 and the contact pins 32a provided in the detecting unit 32 are not in contact with the plate 100. When the plate holder 3 is shifted to the forward direction, the plate 100 is passed above the bar code reading sensors 24 and 25 so that the data of the bar code of two lines depicted on the underside of the plate 100 are read by the bar code reading sensors 24 and 25. Judged from the bar code data read by the bar code reading sensors, if the kind and batch of the plate 100 are the same as those registered in the device and the setting direction of the plate 100 is correct, the motor 18 is immediately reversed and the plate holder 3 is returned to the plate setting position (i.e., solution dropping position) and also the measurement portion 27 is turned back to the horizontal position.

In this state, the pipet 150 containing the test solution and standard solution sucked in the tips 153 and 154 is set in the pipet holder 26 and the test and standard solutions sucked in the pipet 150 are pipetted onto the plate 100. The drops of the test solution and standard solution are respectively filled in the openings 127 and 128 defined in the resist film 120 through the solution feeding holes 142 and 143 defined in the top covering film 140, so that the test and standard solutions are contacted with the ion selective membranes 131 disposed in the holes 121 to 126 formed in the resist film 120. The test and standard solutions filled in the openings 127 and 128 are electrically connected with each other through the solution leading bridge 130. Therefore, there is induced a difference of potential based on the ionic activity of $Na^+$ for example between the terminal portions $Q_1$ and $Q_2$. The pipetting operation of the solutions is detected by the photosensors 160 and 161 shown in FIG. 9 and when it is judged that the pipetting operation is correctly performed on the basis of the detection signals, the motor 18 is driven again after a predetermined time period and the plate holder 3 is shifted in the forward direction.

Figure 12:
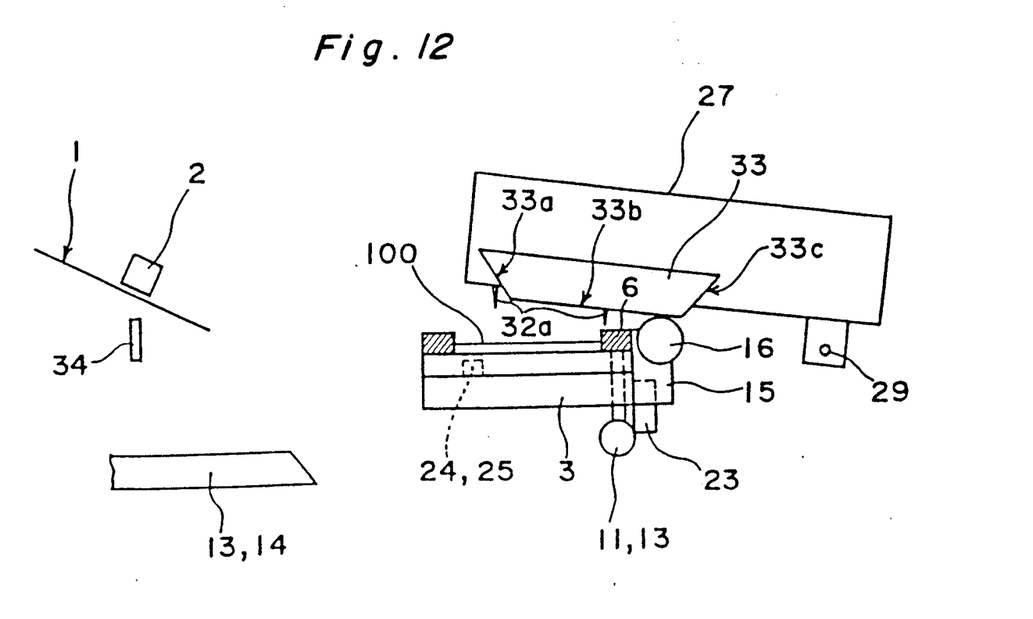
Figure 13:
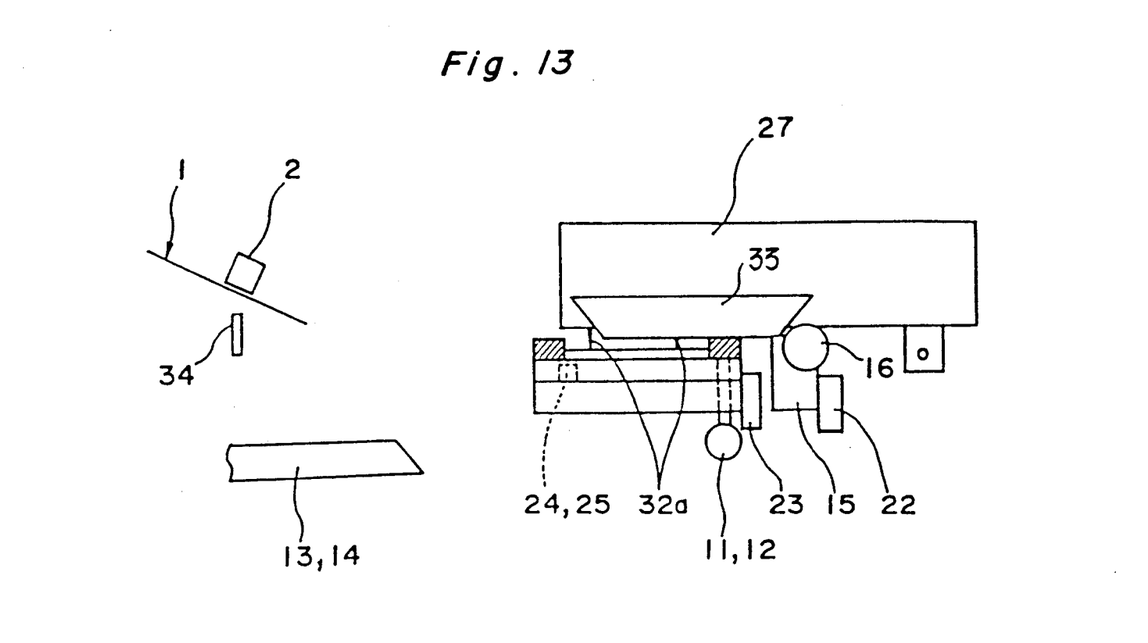
Figure 14:
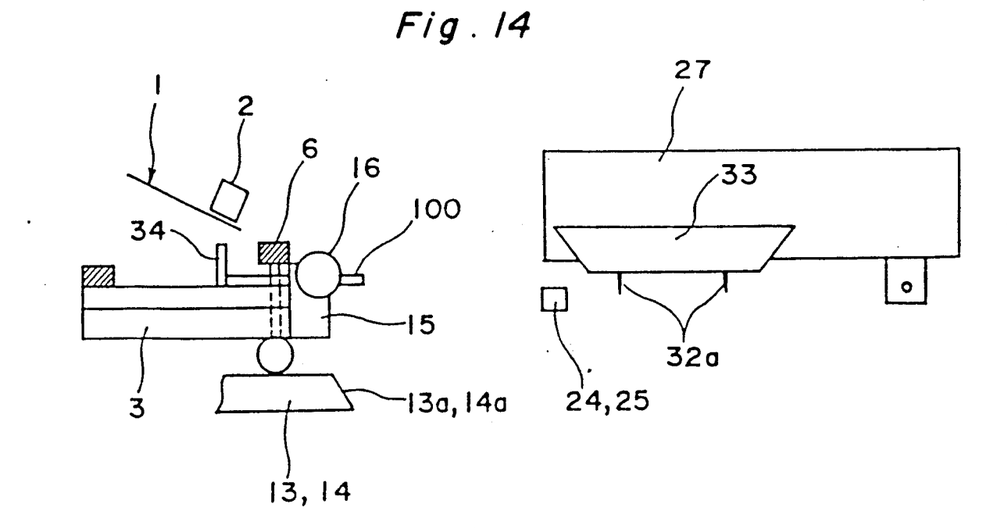

When the plate holder 3 is advanced to the position as shown in FIG. 12, although the plate holder 3 is locked in the measurement position by abutting to the fixing member 23, the lifting member 15 overcomes the biassed force of the spring 17, and when only the lifting member 15 is advanced to be abutted to the fixing member 22, the motor 18 is stopped. In the process of shifting only the lifting member 15, the contact portion of the roller 16 contacted with the cam member 33 is transferred from the flat portion 33b to a second sloped portion 33c so that the measurement portion 27 is set back to the horizontal position. At this time, the contact pins 32a provided in the detecting unit 32 are contacted with the terminal portions $Q_1$ to $Q_6$ disposed in the plate 100 set in the measurement position. As described above, since the plate placing member 3a of the plate holder 3 is depressably held in a floating manner, the contact pins 32a are securely contacted with the terminal portions of the electrodes, so that the differences of potential for the electrodes can be accurately detected. Moreover, when the contact pins 32a are dropped down, since the plate holder 3 is locked in the measurement position, it can be avoided that the contact pins 32a scratch on the surface of the plate 100. When the measurement of the difference of potential is completed, the motor 18 is reversed. Then, only the lifting member 15 is shifted backward so as to be abutted to the front end portion of the plate holder 3, thereafter the plate holder 3 together with the lifting member 15 is shifted backward.

When the plate holder 3 is shifted backward after the completion of the measurement, the plate holder 3 is passed through the plate setting position shown in FIG. 11 and is further shifted backward. In the process of shifting the plate holder 3 backward, the roller 11 and 12 are first abutted onto the sloped surfaces 13a and 14a of the cam members 13 and 14, thereafter the engagement member 6 together with the roller 11 and 12 is lifted up and the front end portion in the forward direction of the plate setting recess 3b is opened. When the plate holder 3 is further shifted backward, the plate removing pin 34 is advanced along the cut slot 3c defined in the plate placing member 3a so as to push the rear end portion of the plate 100 set in the plate setting recess 3b, subsequently, when the plate holder 3 is shifted backward to the plate removing position, the plate 100 is exhausted through the opening formed by lifting the engagement member 6 and the discharged plate 100 is removed through the plate removing shooter 35.

On the other hand, when the data of the bar code are read by the bar code reading sensors 24 and 25 as shown in FIG. 12, in the case that the plate 100 which is not to be measured is set, the plate holder 3 is immediately shifted backward and the plate 100 is removed, and therefore, the wasteful pipetting operation of the solutions can be avoided and also it is not required to disuse the removed plate 100.

As described above, according to the present invention, the plate holder 3 is shifted to predetermined positions by forward and reversely driving the motor 18, and when in the measurement operation, by utilizing the movement of the plate holder 3, the contact pins 32a are shifted up and down and also the plate 100 is exhausted. In other words, since it becomes possible that the series of the operations are controlled by using one motor, the driving mechanism is simplified and also the program for controlling the motor can be simplified.

In addition, in the embodiment of the present invention as mentioned above, although the bar code provided on the underside of the movable plate 100 is read by the bar code reading sensors which are fixed to the device body, another type of bar code reading sensor slidable in the horizontal direction may be used for reading the bar code of the plate 100 set in the plate setting position. Moreover, in the present embodiment, although the test solution and the standard solution are both used so that the ion concentration is detected on the basis of the difference of potential between the test and standard solutions, the ion concentration can be detected by measuring the electric power (or current) generated in the test solution, and also the ion concentration can be detected by measuring the light reflection rate of the test solution dropped in the plate.

In the analyzing device according to the present invention, since the bar code data of the plate can be read before the pipetting operation is performed, in case that a different kind of plate is set or a plate is set in a mistaken direction, such an abnormal condition of the plate can be detected before the pipetting operation of the solution is carried out. Therefore, a wasteful pipetting operation can be prevented, and even if a plate is set by mistake, it is not necessary to disuse the plate, resulting in increased working efficiency.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An analyzing device for measuring a concentration of one or more objecting substances in a test solution based on signals generated due to the drops of said test solution dropped on one or more elements formed on a plate which is disused after once usage thereof or for measuring the concentration based on a difference between a signal generated in the test solution and a signal generated in a standard solution comprises:

plate holding means in which said plate is set in a plate setting position;

plate shifting means for shifting said plate holding means in a predetermined direction so as to set the plate holding means in a pipetting position where the solutions are pipetted in said plate;

bar code reading means for reading bar code data depicted on a predetermined portion of said plate before the pipetting operation is carried out in a pipetting position;

detecting means for detecting the signals based on the drops of the solutions in the plate set in the plate holding means situated in a predetermined position for detecting the signals; and control means for controlling said plate shifting means in such a manner that, when the data of the bar code read by the bar code reading means is not fit for a predetermined measurement condition, the plate holding means is shifted to a plate removing position for removing the plate set in the plate holding means, on the other hand, when the data of the bar code read by the bar code reading means is fit for the predetermined measurement condition, said plate holding means is shifted to the solution pipetting position and after the pipetting operation of the solutions is completed, the plate holding means is further shifted to the measurement position for measuring the detected signals and when the concentration of substance in the test solution is completed by the detecting means, the plate holding means is shifted back to the plate removing position for removing the plate.

2. The analyzing device as defined in claim 1, wherein said bar code reading means are so arranged that the bar code data depicted on the plate can be read in the process of shifting the plate holding means from the plate setting position to the pipetting position by said plate shifting means.

3. The analyzing device as defined in claim 1, wherein said bar code reading means comprises a scanning mechanism for reading the bar code data depicted on the plate set in the plate holding means which is situated in the plate setting position.

4. The analyzing device as defined in claim 1 further comprising warning means for giving a warning signal to an operator and/or means for once stopping the analyzing process when the pipetting operation for pipetting the solutions into the plate set in the pipetting position is not correctly carried out.

5. The analyzing device as defined in claim 1, wherein the shift of said plate holding means is started by said plate shifting means based on the plate detection signals generated from one or more photosensors provide on an plate feeding shooter for setting the plate in said plate holding means which is situated in the plate setting position.

6. The analyzing device as defined in claim 1, wherein said signals generated in the elements of the plate are generated due to a photo conversion and said detecting means is provided for measuring a light reflection rate.

7. The analyzing device as defined in claim 1, wherein said signals generated in the elements of the plate are electric signals and said detecting means is provided for measuring a difference of potential or electric current.

8. The analyzing device as defined in claim 6, wherein said detecting means comprises means for shifting contact members up and down for contacting with the terminal portions of the elements of the plate set in the plate holding means which is stopped.

9. The analyzing device as defined in claim 1 further comprising removing means for removing the plate set in the plate holding means by utilizing the movement when the plate holding means is shifted to the plate removing position.

* * * * *